(12) United States Patent
Gaenger et al.

(10) Patent No.: US 7,279,153 B2
(45) Date of Patent: Oct. 9, 2007

(54) HAIR TREATMENT COMPOSITION CONTAINING A COMBINATION OF THREE DIFFERENT FILM-FORMING HAIR-FIXING POLYMERS

(75) Inventors: Klaus Gaenger, Pfungstadt (DE); Ellen Florig, Grasellenbach (DE)

(73) Assignee: Wella AG, Darmstadt (DE)

( * ) Notice: Subject to any disclaimer, the term of this patent is extended or adjusted under 35 U.S.C. 154(b) by 516 days.

(21) Appl. No.: 10/349,709

(22) Filed: Jan. 23, 2003

(65) Prior Publication Data

US 2004/0146471 A1   Jul. 29, 2004

(51) Int. Cl.
*A61Q 5/06* (2006.01)

(52) U.S. Cl. ............... 424/70.1; 424/70.15; 424/70.22; 424/70.24; 424/70.17; 424/70.11

(58) Field of Classification Search ............... 424/70.1, 424/70.11, 70.15, 70.21, 70.22, 70.31
See application file for complete search history.

(56) References Cited

U.S. PATENT DOCUMENTS

| | | | |
|---|---|---|---|
| 4,402,977 A | | 9/1983 | Grollier et al. |
| 5,266,308 A | * | 11/1993 | Lee et al. ................. 424/70.15 |
| 5,985,295 A | | 11/1999 | Peffly |
| 6,264,929 B1 | * | 7/2001 | Karlen et al. ............... 424/70.1 |

FOREIGN PATENT DOCUMENTS

| | | |
|---|---|---|
| DE | 30 44 754 A1 | 6/1981 |
| DE | 40 34 315 A1 | 5/1992 |
| DE | 43 16 242 A1 | 11/1994 |
| EP | 0 507 896 B1 | 8/1995 |
| EP | 0943312 | 9/1999 |
| WO | 98 19653 | 5/1998 |
| WO | 00 06092 A | 2/2000 |

OTHER PUBLICATIONS

Patent Abstracts of Japan vol. 018, No. 482 (C-1247), Sep. 8, 1994 & JP 06 157249 A Jun. 3, 1994.

* cited by examiner

*Primary Examiner*—Sreeni Padmanabhan
*Assistant Examiner*—Gina Yu
(74) *Attorney, Agent, or Firm*—Michael J. Striker

(57) ABSTRACT

The hair treatment composition for providing a flexible long-lasting hair fixing contains a combination of at least three film-forming, hair-fixing polymers. This hair treatment composition contains at least one amphoteric polymer, at least one anionic polymer and at least one nonionic vinyl lactam homopolymer or copolymer. The at least one amphotenc polymer is formed from at least one monomer, which has at least one neutralized or non-neutmlized acid group, and from at least one other monomer, which has at least one neutralized or non-neutralized amine group. The anionic polymer is built up from at least one radically polymerizable ethylenicaily unsaturated carboxylic acid, such as acrylic or methacrylic acid.

10 Claims, No Drawings

HAIR TREATMENT COMPOSITION CONTAINING A COMBINATION OF THREE DIFFERENT FILM-FORMING HAIR-FIXING POLYMERS

BACKGROUND OF THE INVENTION

The subject matter of the present invention is a hair treatment composition containing a combination of three different film-forming, hair-fixing polymers and indeed with at least one amphoteric polymer, at least one anionic polymer and at least one nonionic vinyl lactam homopolymer or copolymer.

In order to fix and hold human hair or to stabilize an established hairstyle, hair treatment compositions in the form of fixing lotions, aerosols and non-aerosol hair sprays, fixing foams, gels, etc. are used. The hair fixing polymers usually used for cosmetic purposes are characterized by good fixing properties in aqueous, alcoholic or aqueous-alcoholic media. After application to the hair these hair-fixing polymers hold and fix the hair in its shape and stabilize an established hairstyle. However frequently they impart a stiff unnatural feel to the hair, the elasticity of the polymer films is unsatisfactory or the polymer cross-linking is insufficient to provide permanent hold and fixing power is not satisfactory. It is known to combine two polymers to modify the properties of the polymer films.

A composition for hair fixing is known containing a combination of an amphoteric polymer and a nonionic polymer. The combination has good fixing properties with reduced stickiness and good washability from the hair. The duration that the hair is satisfactorily fixed is however frequently unsatisfactory, especially at higher humidity. The softening of the polymer film on the hair caused by high humidity usually causes reduced effectiveness of the hair fixing action when amphoteric polymers are used alone or in the known two-component hair fixing compositions.

SUMMARY OF THE INVENTION

It is an object of the present invention to improve further the film-forming and hair-fixing properties of polymeric hair treatment preparations and especially to increase the elasticity of polymer films and/or polymerically treated hairs and to improve the durability of the positive properties.

It has now been found that this object can be attained by a hair treatment composition with a combination of three different polymers. The hair treatment composition according to the invention contains (A) at least one film-forming, hair-fixing amphoteric copolymer, which is formed from at least one first type of monomer, which has at least one neutralized or non-neutralized acid group, and from at least one second type of monomer, which has at least one neutralized or non-neutralized amine group;

(B) at least one film-forming, hair-fixing anionic polymer; and (C) at least one film-forming, hair-fixing nonionic polymer selected from the group consisting of vinyl lactam polymers and vinyl lactam copolymers.

Film-forming and hair-fixing polymers are, according to the present invention, those polymers, which are in a position to deposit a polymer film on the hair, when used in a 0.01 to 5 percent by weight aqueous, alcoholic or aqueous-alcoholic solution, so that they in this way fix the hair and increase its wave stability. The polymer combination according to the invention imparts good hair fixing with good feel properties, good elasticity and improved permanence.

The amphoteric polymer (A) is contained in the composition according to the invention preferably in an amount of 1 to 15 percent by weight, especially preferably from 2 to 10 percent by weight; the anionic polymer (B), preferably in an amount of 0.01 to 5, especially preferably from 0.02 to 2 percent by weight; and the nonionic polymer (C) is preferably present in an amount of from 0.01 to 5, especially preferably from 0.02 to 2, percent by weight. The amount ratios of the three polymers to each other are selected so that the weight or amount ratio of amphoteric polymer (A) to anionic polymer (B) is preferably from 1:1 to 200:1, especially preferably from 20:1 to 150:1. The amount ratio of anionic polymer (B) to nonionic polymer (C) amounts preferably to 0.5:1 to 2:1, especially preferably of 0.7:1 to 1.5:1.

Suitable amphoteric polymers (A) can be homopolymer or copolymers, which contain cationizable amine groups and also anionic or anionizable acid groups. The cationic and/or cationizable amine groups are either in the polymer chain or preferably are or in substituents in one or more of the monomers. The amphoteric polymer can be copolymerized with neutral comonomers, which contain neither cationic groups nor cationizable groups nor anionic nor an ionizable groups. These neutral comonomers include, e.g. acrylamide, methacrylamide, alkylacrylamides, dialkylacrylamides, alkylmethacrylamides, dialkylmethacrylamides, alkylacrylates, alkylmethacrylates, vinyl caprolactone, vinylpyrrolidone, vinyl caprolactam, vinyl ester, vinyl alcohol, propylene glycol or ethylene glycol. The alkyl groups of these monomers are preferably $C_1$- to $C_7$-alkyl groups, especially preferably $C_1$- to $C_3$-alkyl groups.

The amphoteric polymer can be a copolymer, which is formed from at least one first monomer, which has at least one neutralized or not neutralized acid group and at least one second monomer, which has at least one neutralized or not neutralized basic group. Suitable monomers of the amphoteric polymer, which have acid groups, are unsaturated, radically polymerizable compounds, which carry at least one acid group, e.g. a carboxylic acid group. These monomers especially include carboxy vinyl monomers, such as acrylic acid, methacrylic acid, crotonic acid or maleic acid or their monoesters, of which the acrylic acid and methacrylic acid are especially preferred. Suitable monomers of the amphoteric polymer, which have neutralized or not neutralized basic groups, are unsaturated, radically polymerizable compounds. The basic groups can be primary, secondary or tertiary amines, in which the N-atom also can be part of a ring. For example, copolymers of alkylacrylamide, alkylaminoalkylmethacryate and one, two or more monomers selected from the group consisting of acrylic acid, methacrylic acid and their simple alkyl esters, in which at least one of the monomers carries an acid group, are suitable as the amphoteric polymer. A copolymer of octylacrylamide, N-tertbutylaminoethylmethacrylate and two or more monomers from the group consisting of acrylic acid, methacrylic acid and their alkyl esters, in which at least one of the monomers has an acid group, are preferred amphoteric polymers. Suitable commercial products are AMPHOMER® and AMPHOMERE® LV-71.

Suitable anionic polymers (B) include those polymers, which contain acid groups, such as carboxylic acid groups, sulfonic acid groups or phosphoric acid groups, which are partially or completely deprotonated, e.g., by an organic amine or alkali or alkaline earth hydroxide. The acid groups are preferably 50 to 100% neutralized, especially preferably from 70 to 100% neutralized.

The anionic polymer can be a homopolymer or copolymer with monomer units containing acid groups on a natural or synthetic basis, which is copolymerized with comonomers, which contain acid groups. As acid groups the carboxylic acid groups are particularly preferred. Suitable acid group containing monomers are acrylic acid, methacrylic acid, crotonic acid, maleic acid or maleic acid anhydride, which are partially esterified or hydrolyzed after polymerization. For example, maleic acid monoester, especially the monoester containing from one to seven alkyl groups, as well as aldehydocarboxylic acid or ketocarboxylic acids, are particularly preferred as the acid-group-containing monomer.

Comonomers not substituted with acid groups are, e.g., acrylamide, methacrylamide, alkyl- and dialkylacrylamide, alkyl- and dialkylmethacrylamides, alkylacrylates, alkylmethacrylates, vinyl caprolactone, vinyl pyrrolidone, vinyl caprolactam, vinyl ester, vinyl alcohol, propylene glycol or ethylene glycol, amine-substituted vinyl monomers, such as e.g. dialkylaminoalkylacrylates or -acryl-amides, dialkylaminoalkylmethacrylates or -methyacrylamides, monoalkylaminoalkylacrylates or -acrylamides. The alkyl groups in these comonomers preferably have from one to seven carbon atoms, especially preferably from one to three carbon atoms.

Suitable polymers with acid groups especially include homopolymers of acrylic acid or of methacrylic acid, which are uncrosslinked or crosslinked with polyfunctional agents. Copolymers of acrylic acid or methacrylic acid with selected comonomers are also suitable. The comonomers in these copolymers are preferably acrylic acid- or methacrylic acid esters, acryl amides, methacrylic amides and vinyl pyrrolidones. The suitable polymers also include homopolymers of crotonic acid and copolymers of crotonic acid with certain monomers, such as vinyl esters, acrylic acid esters, methacrylic acid esters, acrylamides and methacrylamides. A suitable natural polymer is, e.g., shellac.

Preferred polymers with acid groups include cross-linked or uncross-linked vinyl acetate/crotonic acid copolymers (INCI name: VA/crotonates copolymer), vinyl acetate/crotonic acid/vinyl alkanoate copolymers (INCI name: VA/crotonates/vinyl propionate copolymer, VA/crotonates/vinyl neodecanoate copolymer), copolymers of one or more $C_1$- to $C_5$-alkyl acrylates, especially $C_2$- to $C_4$-alkylacrylates and acrylic acid or methacrylic acid (INCI name: acrylates copolymers), terpolymers of acrylic acid, alkyl acrylates and N-alkylacrylamides, especially acrylic acid/ethylacrylate/N-t-butylacrylamide terpolymers (INCI name: acrylates/acrylamide copolymer), copolymers of methyl vinyl ether and maleic acid monoalkyl esters (INCI names: ethyl ester of PVM/MA copolymers, butyl ester of PVM/MA copolymers).

The acid groups of the polymers of components (A) and (B) can be partially or completely neutralized with a basic neutralization agent. The preferred neutralization degree is from 50 to 100%, especially preferably from 70 to 100%. The neutralization agent can be an organic or inorganic base. The suitable neutralization agents especially include alkali hydroxides, such as sodium or potassium hydroxide or aminoalcohols, such as 2-amino-2-methyl-1-propanol (AMP), triethanolamine, triisopropanolamine, monoethanolamine, diethanol-amine, tri-(2-hydroxy-1-propyl)amine, 2-amino-2-methyl-2-propan-1,3-diol or 2-amino-2-hydroxymethyl-propan-1,3-diol.

The nonionic polymer (C) can be a homopolymer or copolymer, which is completely or partially built up from vinyl lactam monomers. The preferred vinyl lactams are N-vinylpyrrolidones and N-vinyl captrolactams. Suitable comonomers include vinyl esters, such as vinyl acetate, vinyl alcohol, acrylamides, methacrylamides, alkyl- and dialkylacrylamides, alkyl- and dialkylmethacrylamides, alkylacrylates, alkylmethacrylates, propylene glycol or ethylene glycol, in which the alkyl groups preferably have from one to seven carbon atoms, especially preferably from one to three carbon atoms. For example, monopolymers of vinyl caprolactams or vinyl pyrrolidones are suitable. Additional suitable synthetic film-forming nonionic, hair-fixing polymers are e.g. copolymerizates of vinyl pyrrolidone and vinyl acetate, as well as terpolymers of vinyl pyrrolidone, vinyl acetate and vinyl propionate. Polyvinyl pyrrolidone/vinyl acetate copolymers are particularly preferred.

The composition according to the invention can be packaged in an alcoholic, aqueous-alcoholic or aqueous medium. Alcoholic solvents comprising lower alcohols having from 1 to 4 carbon atoms, such as ethanol and isopropanol, are especially preferred. These lower alcohols can be contained in the compositions in amounts of from 15 to 85, preferably of 25 to 75, percent by weight. Additional organic solvents or a mixture of solvents with a boiling point under 400° C. can be contained in the compositions according to the invention in amounts of from 0.1 to 15, preferably from 1 to 10, percent by weight. Cross-linked and uncross-linked hydrocarbons, such as pentane, hexane, isopentane and cyclic hydrocarbons, such as cyclopentane and cyclohexane, are especially preferred as additional cosolvents. Possible aqueous solvents include glycerol, ethylene glycol and propylene glycol in an amount of up to 30 percent by weight.

The compositions according to the invention can contain the conventional additive ingredients that are known to be suitable for hair treatment compositions, such as wetting agents, emulsifiers or solvating agents, from the classes of nonionic, anionic, cationic or amphoteric surface-active agents in amounts of from 0.1 to 15 percent by weight; moisturizing agents; perfume oils in amounts of from 0.1 to 0.5 percent by weight; plant and vegetable extracts in an amount of from 0.1 to 5 percent by weight; bactericidal and fungicidal agents in an amount of from 0.01 to 1.0 percent by weight; softeners, such as phthalic acid esters, or alkyl citrates, silicone compounds, e.g. volatile or non-volatile silicone oils, high molecular weight siloxane polymers or copolymers of siloxanes and ethylene and/or propylene glycol in an amount of from 0.05 to 20 percent by weight; light protective agents, antioxidants, radical-trapping agents, antiflaking agents, in an amount of about 0.01 to 2 percent by weight; luster-imparting agents, vitamins, combability improving agents, de-fatting agents and antifoaming ingredients, in so far as these additive ingredients are suitable for the respective application forms.

The composition according to the invention can be used in different forms, e.g. as a lotion, non-aerosol spray lotion, which is sprayed by means of a mechanical spraying apparatus, as an aerosol spray which is sprayed by means of a propellant, as a propellant containing aerosol foam components or as a non-aerosol foam composition, which is present in combination with a suitable mechanical apparatus for forming foam, as a gel, as a liquid gel, as a sprayable gel or as a foam gel. Also the composition according to the invention can be in the form of a thickened lotion containing a suitable thickener.

An aerosol hair spray is a preferred embodiment. When the hair treatment composition according to the invention is present in the form of an aerosol hair spray, it contains from 15 to 85 percent by weight, preferably from 25 to 75 percent by weight, of a propellant and is filled in a pressurized container. Lower alkanes, such as n-butane, i-butane and propane, or their mixtures, dimethyl ether, fluorinated hydrocarbons, such as F152a (1,1-difluoroethane) or F134 (tetrafluoroethane) and also propellants present in the form of compressed gases, are suitable as the propellant contained in the aerosol compositions of the invention. Propane and butane are especially preferred as the propellants. The solvent is preferably purely alcoholic, but can also contain up to 10 percent by weight, preferably from 2 to 8, percent by weight water.

An especially preferred aerosol hair spray product comprises a pressurized container, which is filled with a hair spray composition together with a propellant, and spray device for spraying the composition. This composition contains (A) from 1 to 15 percent by weight of an amphoteric copolymer neutralized from 50 to 100 percent, and formed from alkylacrylamide, alkylaminoalkyl-methacrylate and two or more monomers comprising acrylic acid, methacrylic acid and their simple alkyl esters, wherein at least one of the monomers contains an acid group and has an alkyl group containing from one to ten carbon atoms;

(B) from 0.01 to 5 percent by weight of an anionic copolymer neutralized from 50 to 100 percent, and formed from at least one first monomer, which is acrylic acid and/or methacrylic acid, and at least one second monomer, which is an acrylic acid alkyl ester, a methacrylic acid alkyl ester, acrylamide and/or methacrylamide, in which the alkyl groups have from 1 to 5 carbon atoms;

(C) from 0.01 to 5 percent by weight of a vinyl pyrrolidone/vinyl acetate copolymer;

(D) from 10 to 60 percent by weight of a $C_2$- to $C_3$-alcohol; and (E) from 10 to 85 percent by weight of at least one aerosol propellant, preferably propane, butane, dimethyl ether or a mixture of these propellants.

When the hair treatment composition according to the invention is in the form of a sprayable non-aersol hair spray, it is sprayed with the help of a suitable mechanically operated spraying device. A "mechanically operated spraying device" means a device, which sprays the composition without using a propellant. A suitable mechanical spraying device can be, e.g., a spray pump or an elastic container provided with a spray valve, in which the cosmetic composition according to the invention is filled under pressure and from which the composition is continuously dispensed because of contraction of the elastic container when the spray valve is opened.

When the hair treatment composition according to the invention is present in the form of a hair foam composition (mousse), it contains at least one conventional foam-forming substance known for that purpose. The composition is foamed with the help of a propellant gas or a chemical propellant and is worked into the hair as foam and is left in the hair without being rinsed from the hair. The composition according to the invention has an apparatus for foaming the composition as an additional component. An "apparatus for foaming" means a device that produces foam from the composition without using a propellant. A suitable mechanical foam-producing device can, for example, be a commercial foam pump or an aerosol foam head.

When the hair treatment composition according to the invention is present in the form of a hair gel, it also contains at least one gel-form substance in an amount of preferably from 0.05 to 10, especially preferably from 0.1 to 2, percent by weight. The viscosity of the gel amounts preferably to from 500 to 50,000 mPa·s, especially preferably from 1,000 to 15,000 mPa.s at 25° C. (measured with a rotation viscosimeter RheoStress 100 of Haake at a temperature of 25° C. and shear rate of 50 $s^{-1}$).

When the hair treatment composition according to the invention is present in the form of a hair lotion, it is essentially a non-viscous or slightly viscous, flowing solution, dispersion or emulsion containing at least ten, preferably 20 to 95, percent by weight of a cosmetically compatible alcohol. Alcohol suitable for cosmetic purposes comprises lower alcohols having from 1 to 4 carbon atoms, such as ethanol and isopropanol.

The following examples should illustrate the subject matter of the invention in detail, without limiting the appended claims. The polymer content stated in the examples relates to the solid content.

EXAMPLES

Example 1

The following composition A is an example of the hair treatment compositions of the invention. Compositions B, C and D are comparative examples. These four compositions are tabulated in Table I below.

TABLE I

HAIR TREATMENT COMPOSITIONS ACCORDING TO THE INVENTION AND COMPARATIVE COMPOSITIONS

| Ingredient | A | B | C | D |
|---|---|---|---|---|
| Amphomer ®[1] | 4.98 g | 4.98 g | 4.98 g | 4.98 g |
| Ultrahold ® 8[2] | 0.05 g | — | 0.1 g | — |
| PVP/VA Copolymer | 0.05 g | — | — | 0.1 g |
| Aminomethylpropanol | 0.91 g | 0.91 g | 0.91 g | 0.91 g |
| PEG-12 Dimethicone | 0.59 g | 0.59 g | 0.59 g | 0.59 g |
| Perfume | 0.15 g | 0.15 g | 0.15 g | 0.15 g |
| Triethyl citrate | 0.015 g | 0.015 g | 0.015 g | 0.015 g |
| Water | 2.45 g | 2.45 g | 2.45 g | 2.45 g |
| Ethanol | To 100 g | To 100 g | To 100 g | To 100 g |

[1]Octylacrylamide/acrylic acid/butylaminoethylmethacrylate/methylmethacrylate/hydroxypropylmethacrylate copolymer
[2]Ethylacrylate/acrylic acid/N-tert.-butylacrylamide copolymer.

The wave stability (curl retention measurements) of hair strands treated with exemplary composition A according to the invention, with the comparative exemplary composition B and untreated hair strands (in a water wave) was measured. Three uniform standardized groups of counted hair strands were used for each measurement. The counted hair strands in each group had 100 individual hairs (European hair, 16.5 cm long, average diameter of 76.3 µm from Kerling Co.). The measurements were performed on simple bleached hair strands after washing them twice with a standard shampoo (10% sodium lauryl ether sulfate, 4% NaCl). The dried strands at 20° C. and 65% relative humidity were wound on spiral curlers and weighted with a 10 g weight. Then they were treated with 100 µl of the composition to be tested and dried over night at 20° C. and 85% relative humidity. The dried strands were removed or unwound from the rollers, weighted with a 50 mg weight and suspended in an atmosphere with 85% relative humidity at 20° C. The time for the hair locks to stretch to 10 mm was measured.

The following Table II showing the results of the measurements shows that already very slight amounts (only about 0.05 percent by weight) of a combination of anionic and nonionic hair-fixing polymers provide a clear definite extension of the permanence of the hair-fixing action of the amphomer at comparatively high relative humidity (85%). The amounts used (0.05 percent by weight) are so small that a noteworthy increase of fixing strength does not occur. Surprisingly without increase of the fixing strength a definite extension of the fixing duration occurs. Probably in some way the resistance of the polymer film to moisture and/or softening occurs. The holdability or permanence of the standard composition B with only one polymer is doubled in comparison to the untreated hair strands for a 10 mm suspension. The composition A according to the invention shows an additional 89% increase or extension in the hold or permanence of the hair fixing. The two-component compositions C and D only provide slight improvements. The three-component composition A has an unexpected synergistic effect in regard to the extension of hold in comparison to compositions C and D containing two components.

TABLE II

CURL RETENTION MEASUREMENTS FOR A 10 MM SUSPENSION OF TREATED HAIR LOCKS

| | | |
|---|---|---|
| UNTREATED (WATER WAVE) | 2.8 Hours | |
| Composition B: 5% amphoteric polymer | 5.6 Hours | +100% |
| Composition C: 5% amphoteric polymer 0.1% anionic polymer | 6.4 Hours | +129% |
| Composition D: 5% amphoteric polymer 0.1% nonionic polymer | 6.7 Hours | +139% |
| Composition A: 5% amphoteric polymer 0.05% anionic polymer 0.05% nonionic polymer | 8.1 Hours | +189% |

Example 2

Aerosol Hair Spray

The composition A was filled in an aerosol spray can together with a propane/butane propellant mixture in a ratio 67:33.

Example 3

The composition of example 3 was filled in an aerosol spray can together with a propane/butane propellant mixture in a ratio 67:33. The ingredients and proportions of the composition of example 3 are tabulated in Table III below.

TABLE III

HAIR TREATMENT COMPOSITIONS ACCORDING TO THE INVENTION

| Ingredient | Ex. 3 |
|---|---|
| Amphomer ®[1] | 4.98 g |
| Ultrahold ® 8[2] | 0.13 g |
| PVP/VA Copolymer | 0.13 g |
| Aminomethylpropanol | 0.91 g |
| PEG-12 Dimethicone | 0.59 g |
| Perfume | 0.15 g |
| Triethyl citrate | 0.02 g |

TABLE III-continued

HAIR TREATMENT COMPOSITIONS ACCORDING TO THE INVENTION

| Ingredient | Ex. 3 |
|---|---|
| Water | 2.45 g |
| Ethanol | To 100 g |

[1]Octylacrylamide/acrylic acid/butylaminoethylmethacrylate/methylmethacrylate/hydroxypropylmethacrylate copolymer
[2]Ethylacrylate/acrylic acid/N-tert.-butylacrylamide copolymer.

While the invention has been illustrated and described as embodied in a hair treatment composition containing a combination of three different film-forming hair-fixing polymers, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. An alcoholic, aqueous or aqueous-alcoholic hair treatment composition for fixing hair with improved permanence, said hair treatment composition consisting essentially of:
    from 1 to 15 percent by weight of a film-forming, hair-fixing amphoteric copolymer, which is 50 to 100% neutralized and which comprises an alkylacrylamide, an alkylaminoalkylmethacrylate, and two or more monomers, said two or more monomers being selected from the group consisting of acrylic acid, methacrylic acid, alkyl esters of acrylic acid and alkyl esters of methacrylic acid, at least one of the two or more monomers containing an acid group and said alkyl groups in said two or more monomers containing from one to ten carbon atoms;
    from 0.01 to 5 percent by weight of a film-forming, hair-fixing anionic copolymer, which is 50 to 100% neutralized and which comprises at least one first monomer, which is acrylic acid and/or methacrylic acid, and at least one second monomer, which is an acrylic acid alkyl ester, a methacrylic acid alkyl ester, acrylamide and/or methacrylamide, and in which the alkyl groups have from 1 to 5 carbon atoms;
    from 0.01 to 5 percent by weight of a polyvinyl pyrrolidone/vinyl acetate copolymer; and
    a solvent comprising water and/or an alcohol with 1 to 4 carbon atoms, said solvent containing up to 10 percent by weight of said water;
    wherein an amount ratio of said amphoteric copolymer to said anionic copolymer is from 20:1 to 150:1 and an amount ratio of said anionic copolymer to said polyvinyl pyrrolidone/vinyl acetate copolymer is from 0.5:1 to 2:1.

2. The composition as defined in claim 1, wherein said amount ratio of said anionic copolymer to said polyvinyl pyrrolidone/vinyl acetate polymer is from 0.7:1 to 1.5:1.

3. The composition as defined in claim 1, containing from 1 to 10 percent by weight of said amphoteric copolymer, from 0.02 to 2 percent by weight of said anionic copolymer, and from 0.02 to 2 percent by weight of said polyvinyl pyrrol done/vinyl acetate polymer.

4. The composition as defined in claim 1, wherein said amphoteric copolymer is 70 to 100% neutralized with an amino alcohol or with an alkali hydroxide and said anionic copolymer is completely neutralized with said amino alcohol or said alkali hydroxide.

5. The composition as defined in claim 1, further containing from 0.1 to 5 percent by weight of perfume oil.

6. The composition as defined in claim 1, further containing at least one surfactant compound selected from the group consisting of nonionic surface-active agents, anionic surface-active agents, cationic surface-active agents and amphoteric surface-active agents.

7. The composition as defined in claim 1, further containing at least one cosmetic additive ingredient selected from the group consisting of plant extracts, vegetable extracts, bactericidal agents, fungicidal agents, softeners, silicone compounds, light protective agents, antioxidants, radical-trapping agents, anti-flaking agents, luster-imparting agents, vitamins, combability improving agents, de-fatting agents and antifoaming agents.

8. An alcoholic, aqueous or aqueous-alcoholic hair treatment composition for fixing hair with improved permanence, said hair treatment composition consisting essentially of:
 from 1 to 10 percent by weight of an octylacrylamide/acrylic acid/butyl-aminoethylmethacrylate/methylmethacrylate/hydroxylpropyl methacrylate copolymer, which is 50 to 100% neutralized with an amino alcohol or an alkali hydroxide;
 from 0.02 to 2 percent by weight of an ethylacrylate/acrylic acid/N-tert-butylacrylamide copolymer, which is 70 to 100% neutralized with said amino alcohol or said alkali hydroxide; and
 from 0.02 to 2 percent by weight of a polyvinyl pyrrolidone/vinyl acetate copolymer; and
 a solvent comprising a lower alcohol with 2 to 3 carbon atoms and from 2 to 10 percent by weight of water;
 wherein an amount ratio of said octylacrylamide/acrylic acid/butyl-aminoethylmethacrylate/methylmethacrylate/hydroxylpropylmethacrylate copolymer to said ethylacrylate/acrylic acid/N-tert-butylacrylamide copolymer is from 20:1 to 150:1 and an amount ratio of said ethylacrylate/acrylic acid/N-tert-butylacrylamide copolymer to said polyvinyl pyrrolidone/vinyl acetate copolymer is from 0.5:1 to 1.5:1.

9. The composition as defined in claim 8, further containing from 0.1 to 5 percent by weight of perfume oil and at least one surfactant selected from the group consisting of nonionic surface-active agents, anionic surface-active agents, cationic surface-active agents and amphoteric surface-active agents.

10. The composition as defined in claim 8, further containing at least one cosmetic additive ingredient selected from the group consisting of plant extracts, vegetable extracts, bactericidal agents, fungicidal agents, softeners, silicone compounds, light protective agents, antioxidants, radical-trapping agents, anti-flaking agents, luster-imparting agents, vitamins, combability improving agents, de-fatting agents and antifoaming agents.

* * * * *